United States Patent [19]

Horiguichi

[11] Patent Number: 4,779,988
[45] Date of Patent: Oct. 25, 1988

[54] METHOD OF DISTINGUISHING BETWEEN THE FRONT AND BACK SURFACES OF PROCESSED FILM

[75] Inventor: Masashi Horiguichi, Tokyo, Japan

[73] Assignee: Fuji Photo Film Co., Ltd., Kanagawa, Japan

[21] Appl. No.: 919,475

[22] Filed: Oct. 16, 1986

[30] Foreign Application Priority Data

Oct. 18, 1985 [JP] Japan ................................ 60-232717

[51] Int. Cl.$^4$ .......................................... G01N 21/86
[52] U.S. Cl. ................................... 356/445; 356/429; 250/571; 250/572
[58] Field of Search ............... 356/445, 446, 429, 430; 250/571, 572

[56] References Cited

U.S. PATENT DOCUMENTS

| | | | |
|---|---|---|---|
| 2,604,809 | 7/1952 | Mitchell | 356/446 |
| 4,184,082 | 1/1980 | Peoples | 250/572 |
| 4,284,356 | 8/1981 | Heilman | 356/429 |
| 4,456,374 | 6/1984 | Langburg | 356/237 |

FOREIGN PATENT DOCUMENTS 0144447  9/1982  Japan .................... 356/445

Primary Examiner—Bruce C. Anderson
Assistant Examiner—Paul A. Guss
Attorney, Agent, or Firm—Young & Thompson

[57] ABSTRACT

A method of distinguishing between the front and back surfaces of a slide which includes an image on the front surface, comprises reflecting a light beam from each surface of the slide at an acute angle, measuring scattered light around the reflected light beam after the light beam has been reflected repeatedly, and comparing the measurements of the scattered light for the respective surfaces of the slide to detect which of the two measurements is larger. The surface whose measurement is larger is thus determined to be the front surface of the slide.

8 Claims, 3 Drawing Sheets

METHOD OF DISTINGUISHING BETWEEN THE FRONT AND BACK SURFACES OF PROCESSED FILM

BACKGROUND OF THE INVENTION

The present invention relates to a method of distinguishing the front and back surfaces of a processed photographic film.

Processed reversal films (referred to in this specification as films for simplicity) are mounted in cardboard mountings or plastic mountings for use as slides. Commercial laboratories usually return processed slides in cardboard or plastic mountings. It rarely happens in commercial laboratories that the films are mounted in the wrong way.

However, customers sometimes choose to mount films themselves in cardboard or plastic mountings. When this is done, it sometimes happens that films are mounted the wrong way, namely backward.

On occasion, it is necessary to make prints from slides. When making prints from slides mounted backward, the finished prints will show pictures with the right side on the left, namely mirror images.

All of the slide bordered by the mounting must be suitable for projection, and so one must avoid marking either the front or the back surface of the mounted film. As a method of distinguishing the front and/or back surface of film, it is known in the art to measure the difference in reflectance btween the front and back surfaces of a film. This method is based on the fact that the front and back surfaces of film exhibit a difference in reflectivity when wetted with water. For measuring reflectivity by this method, it is required to spray water vapor in the form of steam on both surfaces of the film so that the film will be misted with water.

In this method, however, there is the problem that, since the slides must be wetted well with water for measurement and dried well before printing, a great deal of time is thus spent before printing. Another problem of measurement by this method is that, since the mounting of the slide is unavoidably wetted with steam, the mounting, if it is a cardboard one, is in danger of being torn during the handling of the same. If a slide is held between two transparent glass plates, the slide cannot be subjected to this method.

OBJECTS OF THE INVENTION

It is therefore an object of the present invention to provide a method of distinguishing between the front and back surfaces of film based on the difference in scattering upon reflection, between the front and back surfaces of the films.

It is another object of the present invention to provide a method of distinguishing between the front and back surfaces of films wherein the measurement of the difference in scattering upon reflection between the front and back surfaces of the films can be performed not only without forming any crack or scratch mark on the films but also without tearing the mountings if the films are mounted therein.

It is still another object of the present invention to provide a method of distinguishing between the front and back surface of films which is applicable to films which are held between a pair of glass plates.

It is a further object of the present invention to provide a method of distinguishing between the front and back surfaces of films which can reduce the time required for this purpose.

SUMMARY OF THE INVENTION

In accordance with the present invention, the method comprises reflecting a light beam from each surface of processed film at an angle, measuring the scattered light which surrounds the reflected light beam as a result of the reflection of the light beam, and comparing the resulting measurements of said scattered light reflected from the respective surfaces of the processed film to detect which measurement is larger. Based on the result of this comparison, the surface whose measurement is larger is taken as the front surface of the processed film on which an image has been produced.

According to an embodiment of the present invention, each surface is illuminated by only a single light beam and scattering of reflected light measured by a remote measurement, so that the slides and processed films never get scratch marks and the like. The combination of the use of a light beam and a remote measurement makes it possible to distinguish the front and back surfaces of a slide in a mounting, even with transparent glass covering the same. Furthermore, as there is no necessity to wet the slides with water vapor, no damage such as breakage of their mountings is caused. And as the measurement is executed during movement of the slides, the testing of the slides is rapid and allows saving time before printing.

BRIEF DESCRIPTION OF THE DRAWINGS

Other advantages and objects of the present invention will become apparent when the following detailed description of a preferred embodiment is read in connection with the accompanying drawings, wherein.

DETAILED DESCRIPTION OF THE INVENTION

Figure 1:
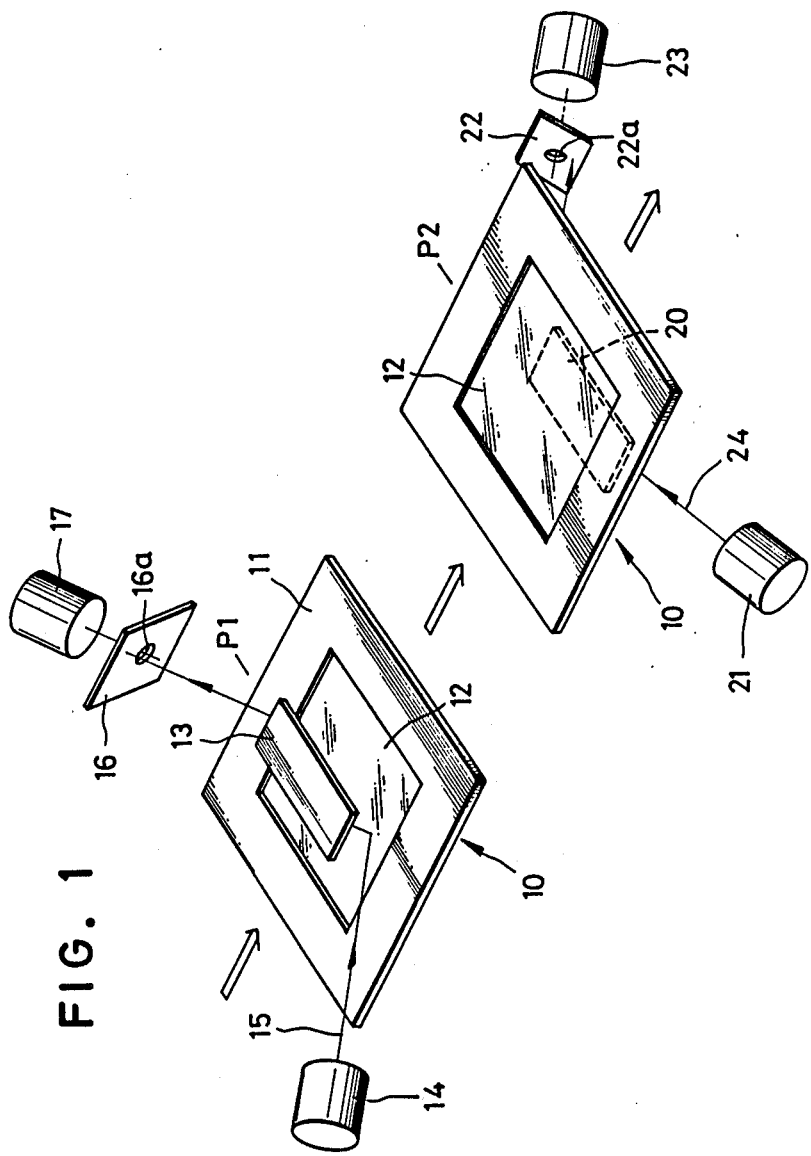
FIG. 1 is a schematic illustration of an apparatus embodying the method of the present invention.

Reference will now be made to FIG. 1 wherein there is illustrated a detecting apparatus embodying the present invention. The apparatus comprises a detecting arrangement at each detecting position P1, P2. The first arrangement at the position P1 comprises a mirror 13 having a reflective surface facing downward and disposed parallel to a virtual plane in which a slide 10 continuously moves in the direction indicated by arrows, a laser 14 disposed to the upper left of the mirror 13 as seen in the figure, a photoelectric element 17 disposed to the upper right of the mirror 13 as seen in the figure, and a diaphragm 16 with a small hole 16a therein. These constructional elements are so arranged that, when the slide 10 is in the illustrated position, the laser beam 15 from the laser 14 impinges on the upper surface of the slide 10 at an angle with respect thereto, is repeatedly reflected between the mirror 13 and the slide 10, and then travels toward the diaphragm 16. However, the diaphragm 16 is so disposed as to block the main reflected laser beam 15, but to allow scattered light surrounding the main beam 15, if in fact the laser beam is scattered, to pass through the hole 16a and impinge on the photoelectric element 17. On the other hand, the second arrangement, which is arranged at the position P2, has just the same construction and functions as the first arrangement except that it is disposed under the virtual plane in order to measure the scattering of light reflected from the back surface of the slide 10.

The slide 10, which comprises a processed reversal film 12 in a cardboard mounting 11, is continuously moved in any well known manner in the direction of the arrows, past the measuring positions P1 and P2. As is well known in the at, the reversal process forms a positive dye image in relief on a gelatin layer of the film 12. The film 12, in general, comprises a film base 12a of cellulose triacetate and a gelatin layer 12b coated the film base 12a (see FIG. 2). As is well known in the art, the reversal processing forms a positive image in relief on the gelatin layer 12b of the film 12. Therefore, the measurement of reflected light from the gelatin layer 12b is very sensitive to the pattern of the image formed on the gelatin layer 12b. In order to compensate the influence of image, however, in this embodiment, the repeated reflections between the mirror 13, 20 and the film 12 is very advantageous. In addition, as a result of this compensation, the S/N ratio, which is a measure of scattering, is increased.

Figure 2:
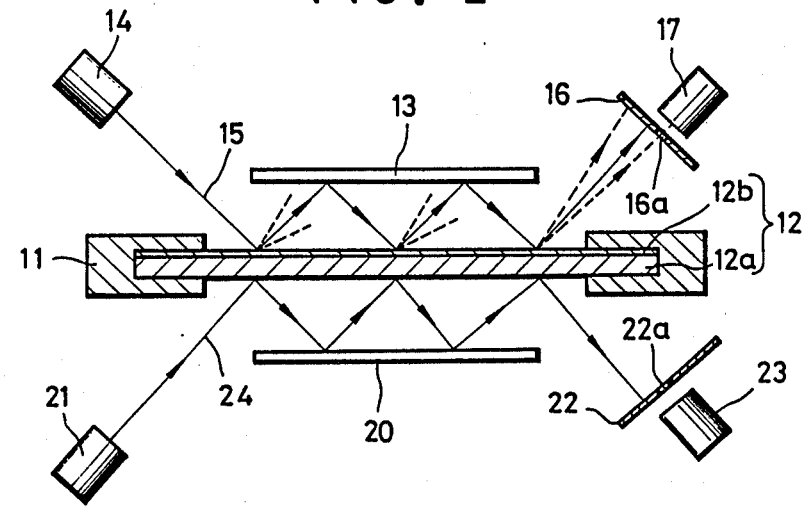
FIG. 2 is an explanatory schematic diagram of the apparatus of FIG. 1 as viewed from front.

Referring to FIG. 2, there is shown a schematic diagram of the apparatus of FIG. 1 as viewed from the front. The film base 12a has a flat and smooth surface, and is capable of reflecting the laser beam 24 with little scattering. Contrary to the film base 12a, the gelatin layer 12b, which is formed with a positive dye image in relief on its surface, scatters the laser beam 15 much more than the film base 12a. Consequently, the intensity of scattered light surrounding the main laser beam after the repeated reflections depends on the surface characteristics of the film 12 by which the laser beam is repeated reflected.

As was previously mentioned, in order to allow only scattered light to impinge on the photoelectric element, each diaphragm 16, 23 is so disposed that the main laser beam 15, 24 misses the hole 16a, 22a. This disposition of the diaphragms 16, 22 ensures that the higher output is always provided from one photoelectric element which receives the light scattered by the gelatin layer 12b than from the other. In the illustrative embodiment in FIG. 2, the photoelectric element 17 has an output higher than that fro the other element 23, because it receives the light scattered by the gelatin layer 12b.

Figure 3:
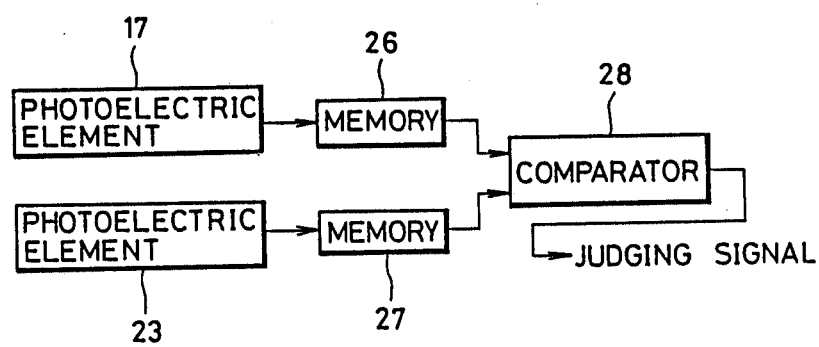
FIG. 3 is a block diagram showing a judging circuit.

Referring now to FIG. 3 there is shown a judging circuit in a block diagram. Outputs from the photoelectric elements 17, 23 are transmitted to memories 26, 27, respectively, for temporary storage. The outputs are later read out and transmitted to a comparator 28 for comparison. The comparator 28 is adapted to judge that the slide 10 is positioned with the gelatin layer 12b, namely the front surface, up in the case of the output stored in the memory 26 being higher than that in memory 27, and vice versa. In accordance with the result of this judgment, the comparator 28 provides a judging signal which desirably gives an indication in either visible or audible form, or both.

Figure 4:
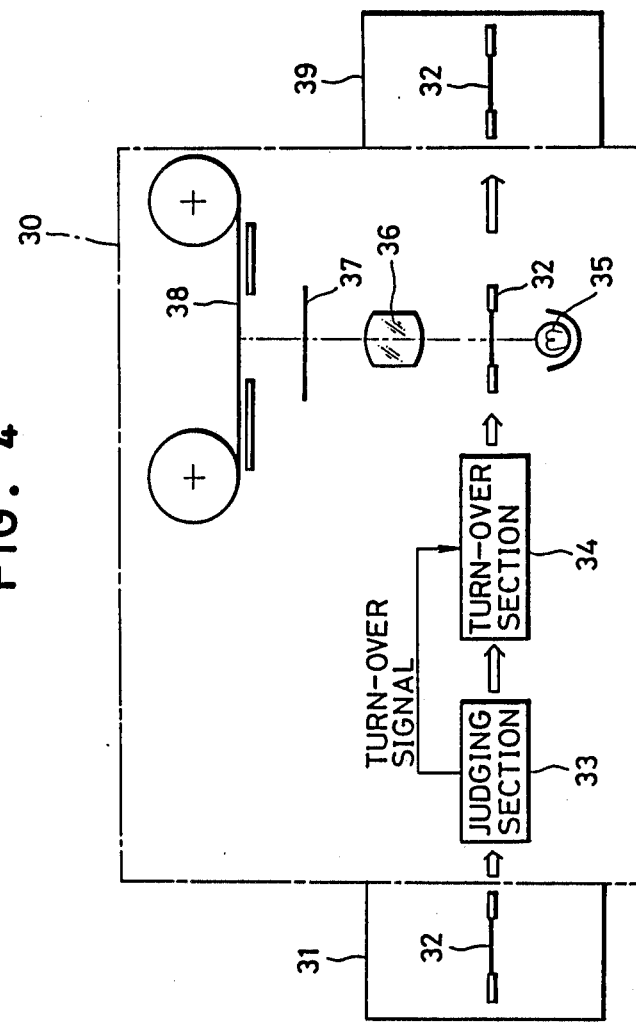
FIG. 4 is a schematic illustration of a slide printing apparatus by which the method of the present invention is practiced.

Reference will now be made to FIG. 4, wherein there is illustrated a slide printing apparatus embodying the method of the present invention. The apparatus comprises a housing 30 and magazines 31 and 39 detachably mounted on opposite sides of the housing 30. In the magazine 31 there is a stack of slides 32 from which prints are to be made and which are withdrawn therefrom one by one to be sent in any well known manner to a judging section 33 including at least the measuring apparatus of FIG. 1 and the judging circuit of FIG. 3 for the detection of the orientation of the slides. A slide 32 is moved through the judging section to pass the measuring positions P1 and P2, successively. At each measuring position P1, P2, as was described above, the light scattered by the surface of the slide 32 is detected by the photoelectric element 17, 23 and output therefrom as an electric signal which in turn is stored in the memory 26, 27. The comparator 28 retrieves the electric signals from the memories 26, 27 to compare the signals with each other in order to judge which signal is stronger. If the signal from the memory 27 is judged to be stronger than the other, that is to say that the slide 32 is disposed upside down, namely, with the back surface (the film base) up, the judging section 33 produces a turn-over signal which in turn is transmitted to a turn-over section 34. Corresponding to the arrival of the slide 32 in the turn-over section 34, the turn-over signal previously transmitted thereto causes the slide to be turned over in any well known manner into the correct position. If there is no turn-over signal transmitted to the turn-over section 34, the slide 34 will pass through the turn-over section 34 without being turned over.

After having passed through the turn-over section 34, the slide 32 is positioned in a printing station and there illuminated by a white light 34 disposed below the printing station. The printing light passes through the slide 32 and travels to a photographic paper 38 after passing through a lens 36 while a shutter 37 is open to form a latent image on the photographic paper 38 in a well known manner. Having completed printing, the slide 32 is moved from the printing station into a storing rack (not shown) inside the magazine 39.

It is permissible in this embodiment to omit one of the detection arrangements in the case of providing a turn-over mechanism at the detection position P1 for turning over slides.

Although the above description has been directed to an embodiment wherein a reversal film is judged as to its orientation, it should be understood that the present invention is applicable with the same result to the detection of the orientation of negative films.

What is claimed is:

1. A method of distinguishing between the opposite surfaces of a processed film, on one said surface an image having been formed, said method comprising:
   reflecting from each said surface of said processed film a light beam having an axis disposed at an acute angle to said surface;
   measuring, only at a location spaced from said axis, scattered light around said light beam as a result of said reflection of said light beam; and
   comparing the measurements of said scattered light from said respective surfaces of said processed film to determine which measurement is greater, thereby determining the surface whose measurement is greater to be said one surface of said processed film.

2. A method as defined in claim 1, wherein said light beam is made to reflect repeatedly from the film.

3. A method as defined in claim 1, wherein said light beam is made to reflect between said surface and a mirror disposed parallel to said surface.

4. A method as defined in claim 3, wherein said light beam is made to reflect repeatedly between said surface and said mirror.

5. A method as defined in claim 1, wherein said light beam is collimated.

6. A method as defined in claim 1, wherein said light beam is a laser.

7. A method as defined in claim 1, wherein said angle is less than 45°.

8. A method as defined in claim 1, wherein said measuring is performed only through a hole in an opaque diaphragm, said hole being spaced from said axis.

* * * * *